US011717172B2

(12) United States Patent
Hermeling et al.

(10) Patent No.: US 11,717,172 B2
(45) Date of Patent: Aug. 8, 2023

(54) METHOD AND SYSTEM FOR DETERMINING A PARAMETER RELATED TO MICROCIRCULATION FUNCTION

(71) Applicant: Stichting IMEC Nederland, AE Eindhoven (NL)

(72) Inventors: Evelien Hermeling, Soerendonk (NL); Eva Wentink, Heeze (NL)

(73) Assignee: STICHTING IMEC NEDERLAND, AE Eindhoven (NL)

(*) Notice: Subject to any disclaimer, the term of this patent is extended or adjusted under 35 U.S.C. 154(b) by 307 days.

(21) Appl. No.: 16/997,908

(22) Filed: Aug. 19, 2020

(65) Prior Publication Data
US 2021/0052169 A1 Feb. 25, 2021

(30) Foreign Application Priority Data
Aug. 20, 2019 (EP) ..................................... 19192512

(51) Int. Cl.
*A61B 5/02* (2006.01)
*A61B 5/318* (2021.01)
(Continued)

(52) U.S. Cl.
CPC .......... *A61B 5/02007* (2013.01); *A61B 5/022* (2013.01); *A61B 5/02125* (2013.01);
(Continued)

(58) Field of Classification Search
CPC . A61B 5/02007; A61B 5/02125; A61B 5/022; A61B 5/02255; A61B 5/053;
(Continued)

(56) References Cited

U.S. PATENT DOCUMENTS 6,908,436 B2 6/2005 Chowienczyk et al.
2004/0092832 A1 5/2004 Schnall et al.
(Continued)

FOREIGN PATENT DOCUMENTS

WO WO 2016/193423 12/2016

OTHER PUBLICATIONS

Nitzan et al. Effects of External Pressure on Arteries Distal to the Cuff During Sphygmomanometry IEEE 52, 6 (Year: 2005).*
(Continued)

*Primary Examiner* — Eric F Winakur
*Assistant Examiner* — Jonathan Drew Moroneso
(74) *Attorney, Agent, or Firm* — Moser Taboada

(57) ABSTRACT

The present invention provides a method (100) for determining at least one parameter related to the microcirculation function of a person, said method comprising the steps of a) determining (101) an arrival time (AT) of a pulse wave, wherein the AT is the time between the onset of an activity of the heart producing said pulse wave and the arrival of said pulse wave in a part of the body of said person; b) varying (102) an applied pressure (P) on said part of the body over time and determining said AT as a function of applied pressure and time; and c) assessing (103) said at least one parameter related to the microcirculation function based on said determination of AT and said AT as a function of applied pressure and time in steps a) and b). The present invention further provides a system (1) for determining at least one parameter.

9 Claims, 4 Drawing Sheets

(51) Int. Cl.
- *A61B 5/021* (2006.01)
- *A61B 5/022* (2006.01)
- *A61B 5/0225* (2006.01)
- *A61B 5/053* (2021.01)
- *A61B 5/00* (2006.01)
- *A61B 5/024* (2006.01)

(52) U.S. Cl.
CPC .......... *A61B 5/02255* (2013.01); *A61B 5/053* (2013.01); *A61B 5/318* (2021.01); *A61B 5/7235* (2013.01); *A61B 5/02416* (2013.01)

(58) Field of Classification Search
CPC ... A61B 5/318; A61B 5/7235; A61B 5/02416; A61B 5/02438
See application file for complete search history.

(56) References Cited

U.S. PATENT DOCUMENTS

| | | |
|---|---|---|
| 2008/0200820 A1 | 8/2008 | Amitzur et al. |
| 2010/0081941 A1* | 4/2010 | Naghavi ............ A61B 5/02007 600/481 |
| 2010/0130876 A1* | 5/2010 | Cho ...................... A61B 5/681 600/490 |
| 2010/0298717 A1 | 11/2010 | Parfyonov et al. |
| 2011/0152699 A1 | 6/2011 | Cho |
| 2015/0359437 A1* | 12/2015 | Maltz .................. A61B 5/6828 600/481 |
| 2019/0298188 A1* | 10/2019 | Dana .................. A61B 5/02116 |
| 2020/0390338 A1* | 12/2020 | Ozawa .................. A61B 5/022 |
| 2022/0061687 A1* | 3/2022 | La ...................... A61B 5/02255 |

OTHER PUBLICATIONS

Allen et al., "Photoplethysmography and its application in clinical physiological measurement", Physiological Measurement, vol. 28, 2007, pp. R1-R39.

Song et al. "Estimation of Blood Pressure Using Photoplethysmography on the Wrist" Computers in Cardiology 2009, vol. 36: pp. 741-744.

Uangpairoj et al., "Evaluation of vascular wall elasticity of human digital arteries using alternating current-signal photoplethysmography", Vascular Health and Risk Management, vol. 9, 2013, pp. 283-295.

Wu et al., "Assessment of Vascular Health With Photoplethysmographic Waveforms From the Fingertip", IEEE Journal of Biomedical and Health Informatics, vol. 21, No. 2, Mar. 2017, pp. 382-386.

* cited by examiner

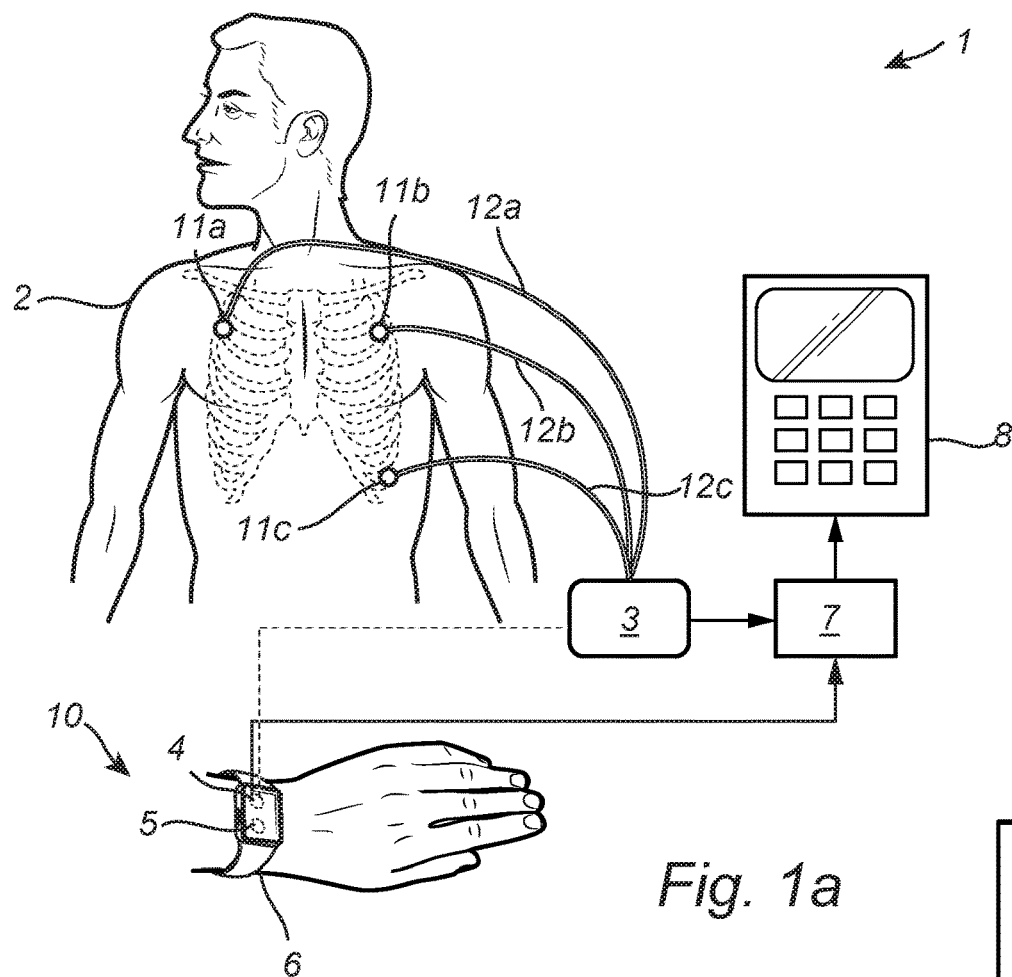
Fig. 1a
Fig. 1b
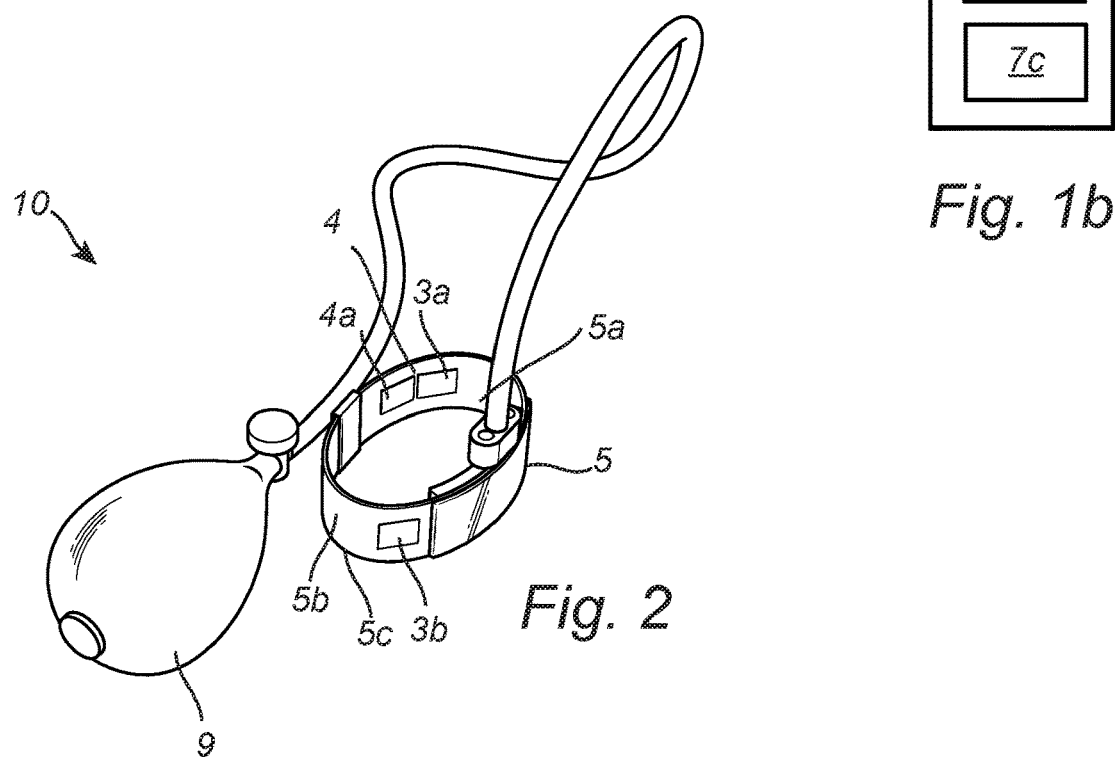
Fig. 2

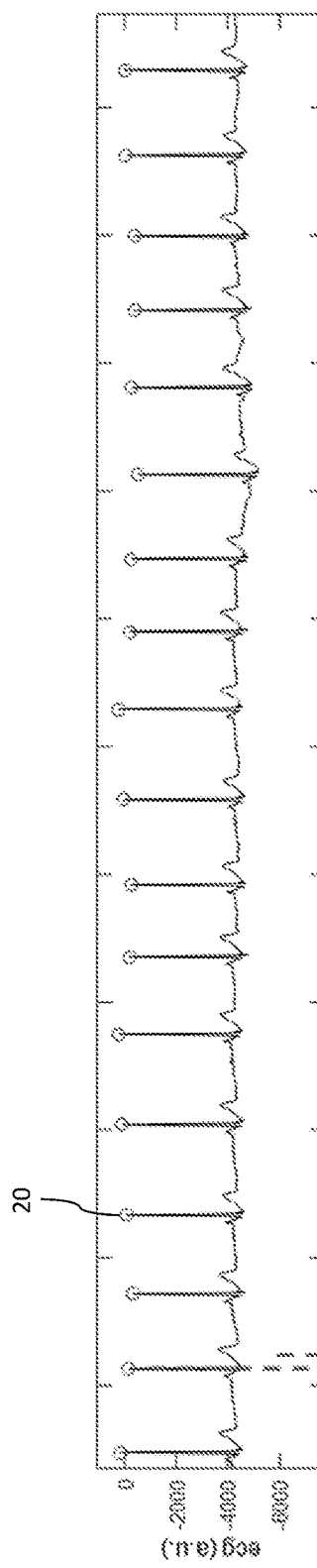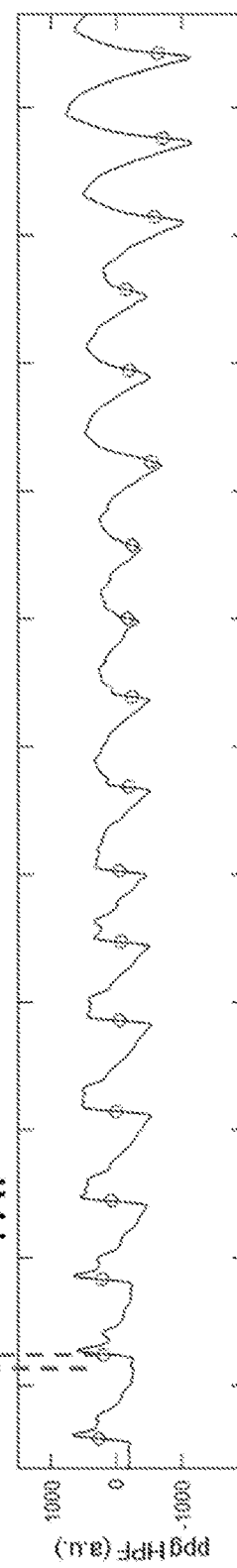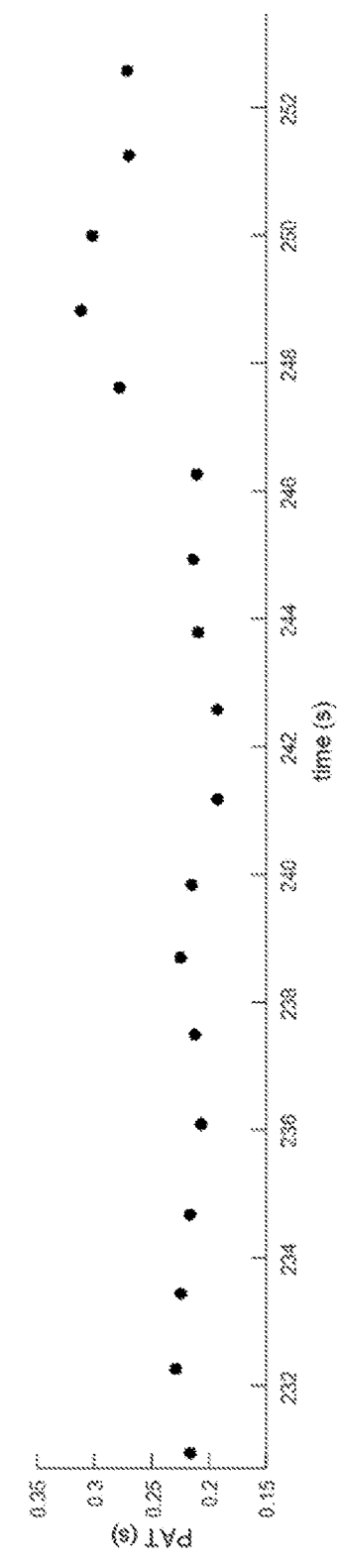
Fig. 3a
Fig. 3b
Fig. 3c

METHOD AND SYSTEM FOR DETERMINING A PARAMETER RELATED TO MICROCIRCULATION FUNCTION

CROSS-REFERENCE TO RELATED APPLICATIONS

This application claims priority to the European Patent Application No. 19192512.2 filed on Aug. 20, 2019, which is hereby incorporated by reference in its entirety.

TECHNICAL FIELD

The present inventive concept relates to the field determining microcirculation functional parameters of a person. More particularly it relates to a method and a device for enabling assessing endothelial function in the microvasculature.

BACKGROUND

Functional diagnostics allows for early detection of cardiovascular diseases. Endothelium is the inner cell layer in blood vessels, that forms the interface between circulating blood and the vessel wall. It has several important functions namely: barrier function between vessel lumen and surrounding tissue, controlling materials and white blood cells in and out of the bloodstream, blood clotting function as the endothelial layer acts under healthy conditions as a non-thrombogenic surface and control of blood pressure by vasoconstriction and dilatation. The loss of these functions, called endothelial dysfunction, is a hallmark for vascular diseases. It is often seen in patients with atherosclerosis, coronary artery disease, diabetes mellitus, hypertension and hypercholesterolemia.

Current methods for determining endothelial function are for example invasive procedures such as coronary epicardial vasoreactivity and venous occlusion plethysmography and nitroglycerine induced vasodilation, which requires infusion of nitroglycerine. Another method is endothelial peripheral arterial tone (EndoPAT), which measures the difference between left and right PPGs (photoplethysmogram) but is however not suitable for determining the endothelial function in the microvasculature. Thus, current methods that are used to assess endothelial dysfunction are either, invasive, require administration of certain drug, require highly trained personnel or expensive equipment. In addition, these methods are mainly applicable to large arteries.

US20100298717 A1 discloses a method for non-invasively determining the endothelial function comprising measuring the amplitude of a plethysmographic signal in an extremity at various pressures and then lowering the pressure to a predetermined percentage of the maximal amplitude. Finally, an occlusion test is performed for at least five minutes. After the occlusion test, the recorded plethysmographic signal is analysed.

However, there is a need in the art for improved or alternative methods for determining microcirculation function, such as endothelial function, of a person.

SUMMARY

It is an object of the invention to at least partly overcome one or more limitations of the prior art. In particular, it is an object to provide a method and a device for enabling assessing of microcirculation function, such as endothelial function in the microvasculature.

As a first aspect of the invention, there is provided a method for determining at least one parameter related to the microcirculation function of a person, said method comprising the steps of
a) determining an arrival time (AT) of a pulse wave, wherein the AT is the time between the onset of an activity of the heart that produces said pulse wave and the arrival of said pulse wave in a location at a microvasculature in a part of the body of said person;
b) varying an applied pressure (P) on said part of the body over time, wherein the applied pressure compresses at least tissue surrounding the location at the microvasculature in the part of the body, and determining said AT as a function of applied pressure and time; and
c) determining said at least one parameter related to the microcirculation function based on said determination of AT and said AT as a function of applied pressure and time in steps a) and b).

The first aspect of the invention is based on the insight that different parameters related to microcirculation function may be determined by measuring the arrival time (AT) of a pulse wave from the heart to the microcirculation while inducing external pressure changes to the tissue under investigation.

The pulse wave could be a blood pulse wave.

The method is advantageous in that it provides for a non-invasive method for determining the parameter or parameters related to the microcirculation function of a person. The method of the first aspect is further easy to use, in contrast to alternative methods, such as flow-mediated dilation methods (FMD), since it does not require an expert to measure and analyze data. Moreover, the method provides for measuring e.g. endothelial function of arterioles and capillaries and not large conduit arteries.

The part of the body of the person is the part under investigation. The part of the body may be an extremity or any tissue that allows for compression. As an example, the tissue or extremity may be selected from finger, wrist and ankle.

Thus, the applied pressure in step b) may be an external applanation pressure.

The at least one parameter related to the microcirculation function that are determined using the method may be used in a diagnosis for cardiovascular diseases (CVD) at an early stage. The method of the first aspect of the invention may thus be a noninvasive method for determining one or several endothelial function parameters of the person. The method of the first aspect may thus be used in the assessment of endothelial function or dysfunction in considered healthy subjects and patients with for instance diabetes mellitus, hypertension or atherosclerosis.

Step a) may be regarded as a substep of step b). Thus, steps a) and b) may be performed simultaneously.

Steps a) and b) may in total be performed for at least 30 s, such as at least 60 s.

In embodiments of the first aspect, steps a) and b) are performed simultaneously during a time period that is at least 60 s, such as at least 100 s, such as at least 200 s.

In embodiments of the first aspect, steps a) and b) are performed simultaneously during a time period that comprises a plurality of heartbeats of the person.

In embodiments of the first aspect, step b) is performed such that at least 10 data points, such as at least 25, such as at least 50 data points of the AT as a function of time is determined. Such data points may include determination of the AT at both increased and decreased applied external pressures.

In embodiments of the first aspect, step a) comprises the steps of a1) acquiring information about the onset of an activity of the heart that produces a pulse wave in said person as a function of time; and a2) acquiring information about the arrival of said pulse wave in the location at the microvasculature in the part of the body as a function of time during step a1); and a3) determining the AT from the information from step a1) and a2).

Step a1) is thus for acquiring information of the start of a pulse wave or a plurality of pulse waves, whereas step a2) is for acquiring information when the pulse wave or plurality of pulse waves have reached the part of the body under investigation. The AT may then be calculated from the information about the start time and the arrival time of the pulse waves.

As an example, step a1) may comprise acquiring an electrocardiogram (ECG) of said person. The ECG, or EKG, refers to the diagram produced during electrocardiography and comprises a recording of the voltage versus time of the electrical activity of the heart. An ECG may be acquired using electrodes placed on the skin of the person being investigated. The ECG of a heart in a normal sinus rhythm may comprise a QRS complex, i.e. the main spike seen in the ECG diagram, corresponding to the depolarization of the right and left ventricles of the heart and contraction of the large ventricular muscles.

The onset of an activity of the heart measured in step a1) may be the onset of electrical activation, such as a Q or R peak detection.

The Q peak may thus be the peak of the deflection immediately following the P peak, whereas the R peak may be the main peak of the ECG of a normal heart, i.e. the peak of the upward deflection following the Q deflection.

Consequently, the AT determined in step a3) may be the pulse arrival time (PAT), wherein the PAT is the time delay between onset of electrical activation in the ECG and the arrival of the pulse wave in said part of the body.

As a further example, step a1) may comprise acquiring an impedance cardiogram (ICG) of said person. An ICG refers to the information acquired during impedance cardiography measuring total electrical conductivity of the thorax. An ICG may be acquired using electrodes for measuring impedance changes caused by low magnitude current flowing through thorax.

As an example, the onset of an activity of the heart measured in step a1) may be the opening of the aortic valve, such as the B-point of the ICG. The B-point of the ICG refers to the onset of the increase in ICG signal, when the blood is suddenly ejected from the left ventricle to the aorta.

Consequently, the AT determined in step a3) may be the pulse transit time (PTT), wherein the PTT is the time delay between opening of the aortic valve and the arrival of the pulse wave in said part of the body.

As a second example, the onset of an activity of the heart measured in step a1) may be measurement of arrival of the pulse wave of proximal blood vessel to the part of the body under investigation. The arrival of the wave proximal to the part of the body under investigation can be measured with a pressure or piezo sensor or photopletysmogram (PPG). Consequently, the AT determined in step a3) may be the pulse transit time (PTT), wherein the PTT is the time delay between arrival of the pulse wave at a proximal blood vessel and the arrival of the pulse wave in a distal part of the body. The distal part of the body is further away from the heart than the proximal blood vessel.

In embodiments of the first aspect, step a2) comprises acquiring a plethysmogram at said part of the body of said person.

A plethysmogram gives information about volume changes of an organ due to e.g. fluctuations in the amount of blood. The plethysmogram may be a photoplethysmogram (PPG), which is an optically obtained plethysmogram used for determining changes in blood volume in the microvasculature, such as in an extremity, such as in a finger. A PPG may thus be used to determine the arrival of the pulse wave at the extremity under investigation. Step b) may thus comprise continuously acquiring a PPG while varying an applied pressure on the extremity, and based on information from step a), the arrival time (AT) may be determined as a function of time during different applied pressures.

Step a2) may also be performed using e.g. Doppler flowmetry.

The pressure applied in step b) may for example be performed using an inflation device surrounding the part of the body at the location in the microvasculature in which the arrival of the pulse wave is determined, such as surrounding the extremity. Thus, the pressure applied in step b) may be applied by using a pressure cuff.

As an example, step b) may comprise applying external pressure for at least one period, wherein said period consists of an increase in applied pressure and a resting phase.

The length of the resting phase may be determined by the recovery time of the tissue under investigation.

The external pressure may thus be applied during a period that is at least 10 s, such as at least 30 s, such as at least 40 s.

Step b) may also comprise applying a constant pressure for a period of time, such as during at least one heartbeat of the person being investigated, such as during at least 1 s.

As an example, step b) may comprise applying external pressure over a time course during which plurality of pulse waves arrives at said part of the body.

Step b) may comprise applying pressure in a plurality of periods at a frequency such that the vascularity is stabilized between the periods. The frequency may be less than one pressure period per minute.

Consequently, step b) may comprise determining AT as a function of applied pressure and time during a plurality of pressure periods, such as during at least two, such as at least three applied pressure periods.

Further, step b) may comprise applying a constant or no pressure between the applied pressure periods.

Step c) may comprise determining at least one endothelial function parameter from the information acquired from performing step a) and step b). The at least one endothelial function parameter may be at least one parameter selected from the group consisting of the average pulse transit time from arteries to capillaries ($PTT_{art-cap}$), the pulse transit time overshoot ($\Delta PAT$), the pressure in capillary ($P_{cap}$) and the dynamical response time constant ($t_{RC}$) of the arrival time of the pulse wave.

Thus, in embodiments of the first aspect, step c) comprises determining an average pulse transit time from arteries to capillaries ($PTT_{art-cap}$), wherein $PTT_{art-cap}$ is the average AT determined in step b) when no pressure is applied to said part of the body minus the average AT from step b) at an applied maximum possible capillary pressure, such as a pressure of at least 50 mmHg.

In embodiments of the first aspect, step c) comprises determining a pulse wave transit time overshoot ($\Delta AT$); wherein $\Delta AT$ is the highest observed AT while decreasing said applied pressure in step b) minus the average arrival time when no pressure is applied in step b).

In embodiments of the first aspect, step c) comprises determining the pressure in capillary ($P_{cap}$), and wherein $P_{cap}$ is the applied pressure in the part of the body at which the arrival time of said pulse wave is highest.

In embodiments of the first aspect, step c) comprises determining a dynamical response time constant ($t_{RC}$) of the arrival time of the pulse wave by fitting an exponential decay function to the AT as a function of time during decrease of said applied pressure.

As a second aspect of the invention, there is provided a system for determining at least one parameter related to the microcirculation function of a person, said system comprising a first device for measuring the onset of an activity of the heart that produces a pulse wave in said person;

a second device for measuring arrival of the pulse wave in a microvasculature in a part of the body of said person, wherein the first and second devices are synchronized with each other;

a pressure device for applying a pressure on said part of the body of said person; and a control unit configured to receive information from said first device, second device and said pressure device and to further configured to perform the method according to the first aspect discussed above.

This aspect may generally present the same or corresponding advantages as the former aspect. Effects and features of this second aspect are largely analogous to those described above in connection with the first and second aspects. Embodiments mentioned in relation to the first aspects are largely compatible with the second aspect.

The system of the second aspect may be used as an automatic control system for monitoring parameters related to the microcirculation function of a person, such as endothelial function parameters of a person. The determination of microcirculation function is performed by the control unit and is based on the output readings from the first device, the second device and the pressure device.

The first and second devices are synchronized with each other. This means that they may be configured to be operated by the same timing device. Thus, in embodiments, the system comprises a timing device, such as a clock, for synchronizing the first and second devices.

The second device may be configured to measure arrival of the pulse wave in a location at the microvasculature in a part of the body of the person and the pressure device may be configured to apply pressure to compress at least the tissue surrounding the location at the microvasculature in the part of the body.

In embodiments of the second aspect, the first and second devices are arranged together in a single unit. As an example, the first and second units may be arranged in the same wrist band.

Having the first and second devices arranged in a single unit or device may increase the possibility of a tight synchronization between the devices.

Furthermore, in embodiments, the second device and the pressure device are arranged in the same unit, such as in a wrist band, a finger cuff or finger band.

In embodiments, the first device, the second device and the pressure device are all arranged in a single unit, such as in a wrist band, a finger cuff or finger band.

The control unit may be wiredly connected to the first and second device and to the pressure device. As an alternative, the control unit may be wirelessly connected to the first and second device and to the pressure device. The control unit may be configured to synchronize the first and second devices.

The control unit is for analysing the data acquired by the first device, the second device and the pressure device. Thus, the control unit may comprise computer program products configured for performing the method steps of the first aspect described above The control unit may comprise a processor and communication interface for communicating with the first device, the second device and the pressure device and thus for receiving information from these devices.

The control unit may also be configured for controlling when to take measurements with the first and second devices of the system and when to apply a pressure using the pressure device.

In embodiments of the second aspect, the control unit is further configured for controlling the initiation of the measuring of said first and second devices and the initiation of the applying of a pressure of said pressure device and further configured for receiving information of the onset of an activity of the heart from said first device, information of changes in arrival time from said second device and information about applied pressure on said extremity from said pressure device.

Hence, the control unit may further comprise computer program products configured for sending operational requests to said first and second devices and to said pressure device. The operational requests may be based on analysis of received data from these devices or according to a preprogrammed operational scheme. For this purpose, the control unit may comprise a processing unit such as a central processing unit, which is configured to execute computer code instructions which for instance may be stored on a memory.

In embodiments of the second aspect, the first device is a device for acquiring an electrocardiogram (ECG), an impedance cardiogram (ICG) or a pulse wave at a proximal blood vessel of said person.

Thus, the first device may be an electrocardiographic machine comprising a plurality of electrodes for attachment to the skin of a person. These electrodes may be connected to a central processing unit of the electrocardiographic machine.

The first device may also be a device for acquiring an ICG comprising a plurality of electrodes for attachment to the skin of a person, such as to the thorax region of the skin. The device for acquiring an ICG may further be configured for transmitting a low magnitude alternating current to these electrodes and also be configured for measuring an impedance to the transmitted current. The first device may also be a pulse wave device comprising a pressure, piezo, or photoplethysmogram (PPG) sensor.

In embodiments, the electrocardiographic machine is also configured for acquiring an ICG of a person, i.e. the electrodes of the electrocardiographic machine may also be used for measuring the impedance to an applied current.

In embodiments of the second aspect, the second device is a device for acquiring a plethysmogram, such as a photoplethysmogram (PPG), of a person.

The device for acquiring a PPG may comprise at least one sensor for measuring changes in light absorption in the skin. The device may thus comprise a light source for illuminating the tissue of the person being investigated and a photodiode for measuring changes in light absorption of the illuminated light by the tissue in the extremity. The device may thus be a pulse oximeter. The PGG may be obtained by measuring a transmissive absorption or a reflection of the illuminated light.

The pressure device may be configured for creating a mechanical pressure on the extremity of a person under investigation. In embodiments of the second aspect, the pressure device is a pressure cuff for compressing an extremity of a person. However, the pressure device may alternatively apply pressure at another part of the body, such as being arranged in a patch to apply pressure on the torso.

The pressure cuff may be a manual pressure cuff e.g. comprising a manual pump for generating the pressure in an inflatable cuff, e.g. the same as used when measuring the blood pressure. The pressure cuff may thus be a sphygmomanometer. The pressure cuff may as an alternative be an electronic cuff, i.e. configured for generating the pressure as a response to an electronic signal.

The pressure cuff may be arranged to surround an extremity of the person during investigation. The pressure cuff may thus be arranged to surround e.g. a wrist, an arm or a leg of a person.

As an example, the pressure cuff may surround the device for acquiring a photoplethysmogram (PPG). The pressure cuff and the device for acquiring a PPG may thus be kept in tight synchronicity. The pressure cuff and the device for acquiring a PPG may thus be in the same unit. The pressure cuff may thus be arranged for surrounding an extremity of a person and may comprise an inner surface and an outer surface. The inner surface may be for contacting the person when surrounding the extremity and the device for acquiring a PPG may thus be arranged on the inner surface. In an embodiment, the system may comprise a band configured to be arranged around the part of the body of the person, wherein the device for acquiring an PPG is arranged at an inner surface of the band and wherein the band comprises inflatable portions incorporating the device for acquiring an PPG.

Further, the system may also comprise display means configured for displaying any determined endothelial function parameter for an operator or for the person being investigated. The display means may for example comprise a flat panel display, such as a LED display.

As a third aspect of the invention, there is provided a method for determining at least one parameter related to the microcirculation function of a person comprising the steps of i) receiving data of the arrival time (AT) as a function of time and applied pressure; wherein the AT is the time between the onset of an activity of the heart that produces a pulse wave in a person and the arrival of said pulse wave in extremity part of the body of said person and wherein said applied pressure is a pressure applied to said part of the body, and ii) determining at least one parameter related to the microcirculation function from said received data.

The data received in step i) may be data earlier obtained from a person being investigated. The method of the third aspect may thus be an evaluation method carried out after having retrieved the required data. The method of the third aspect may be performed at a location remote from any system used for retrieving the data and at a later time point.

The data received in step i) may be data obtained performing the steps a) and b) of the method according to the first aspect above. Further, the data received in step i) may be data obtained using the system according to the second aspect above.

In embodiments of the third aspect of the invention, the data comprises AT as a function of time during at least one applied pressure period, wherein said period consists of an increase in applied pressure and a resting phase.

The method for determining at least one parameter related to the microcirculation function of a person described above may be embodied as a computer program product comprising a computer-readable storage medium with instructions adapted to carry out the inventive method when executed by a processor. The processor may be any kind of processor, e.g., a central processing unit (CPU), a graphics processing unit (GPU), a custom made processing device implemented in an integrated circuit, an ASIC, an FPGA, or logical circuitry including discrete components.

Consequently, as a fourth aspect of the invention, there is provided a computer program product comprising a computer-readable storage medium with computer code instructions adapted to carry out the method of the third aspect when executed by a device having processing capability.

The computer-readable storage medium may be any tangible medium that may facilitate transport of the computer program product. For instance, the computer-readable medium may be a portable physical memory, such as a universal serial bus (USB) stick, a compact disc (CD) or a digital versatile disc (DVD). The computer program product may also or alternatively be stored on a memory, such as a random access memory (RAM) or a read-only memory (ROM), which may be accessible to a processing unit of a computer.

According to another aspect, there is thus provided a computer comprising a processing unit and a memory, which stores the computer code instructions of the computer program product of the fourth aspect. The computer may thus be provided with functionality for allowing determination of at least one parameter related to the microcirculation function of a person.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

FIG. 1a is an illustration of a system for assessing at least one parameter related to the microcirculation function of a person.

FIG. 1b is a schematic illustration of a control unit.

FIG. 2 is an illustration of a combined ECG and PPG device with pressure cuff.

FIGS. 3a-c show schematic illustrations of how PAT may be calculated from ECG and PPG signals and plotted as a function of time.

DETAILED DESCRIPTION

Figure 4:
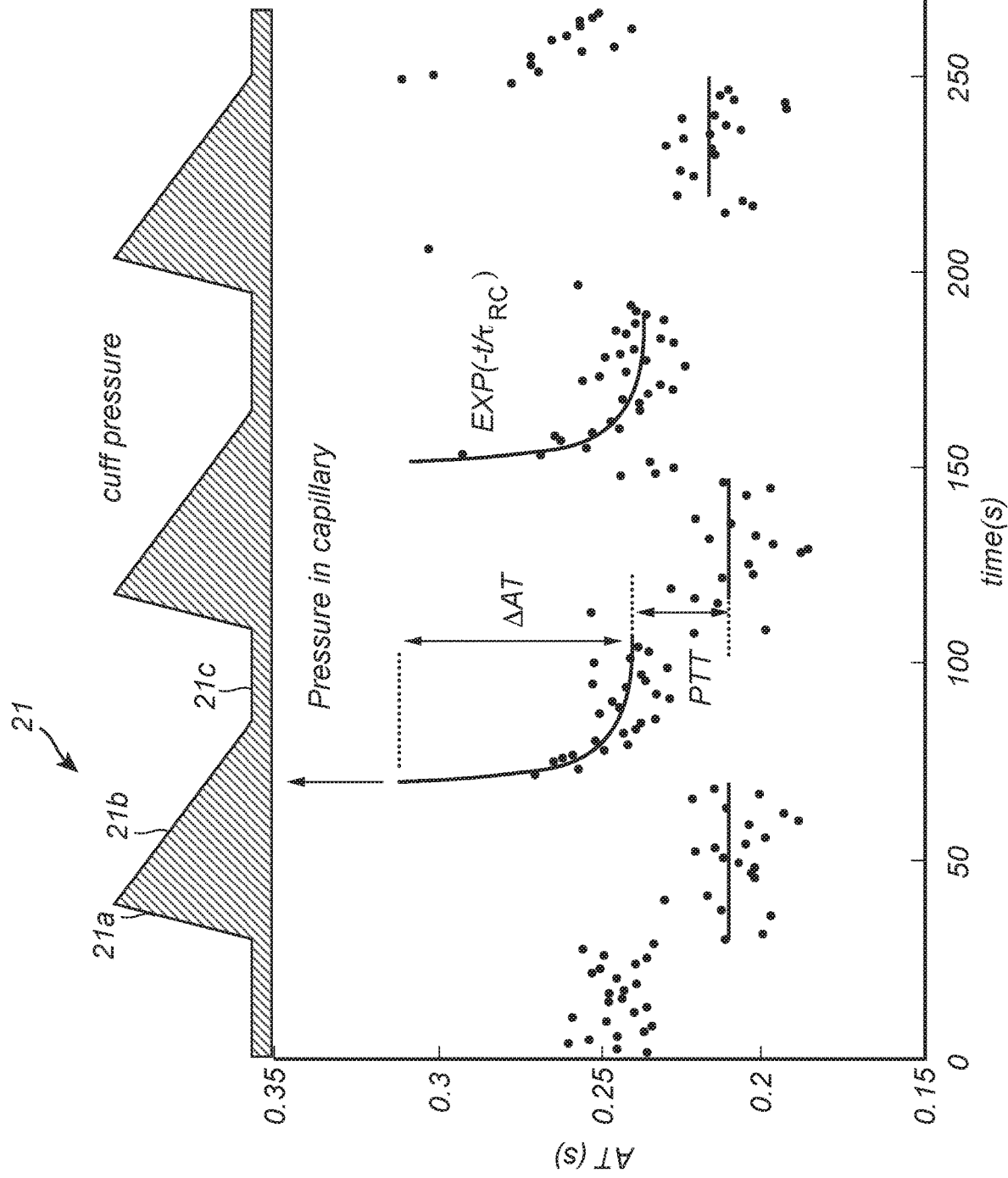
FIG. 4 schematically illustrates how to asses endothelial function parameters from acquired data of PAT as a function of time at different applied pressures.

FIG. 1a is an illustration of a system 1 for determining at least one parameter related to the microcirculation function, such as at least one endothelial function parameter, of a person 2. The system comprises a first device 3 for measuring the onset of an activity of the heart that produces a pulse wave in the person 2 under investigation. The first device 3 is in this example a device for acquiring an electrocardiogram (ECG) and comprises three electrodes 11a, 11b and 11c arranged for being attached onto the skin of the person 2.

The system 1 further comprises a second device 4 for measuring arrival of the pulse wave in a part of the body of the person 2. In this example, the second device 4 is for measuring the arrival of the pulse wave at the wrist of said person 2. The system 1 further comprises and a pressure device 5 for applying a pressure on the wrist of the person 2.

In this example, the device 4 for measuring arrival of the pulse wave is a device for acquiring an photoplethysmogram (PPG) of the person 2, hereinafter called the PPG device 4, whereas the pressure device 5 is a pressure cuff for compressing an extremity of the person, in this embodiment for compressing the wrist 6 of the person 2.

The ECG sensor 3 is tightly synchronized with the PPG sensor 4, such as configured to be operated by the same timing device (not shown). This is illustrated by the dotted line in FIG. 1a.

The pressure cuff 5 and the PPG device 4 may be arranged in the same apparatus 10 for combined PPG measurements and pressure application, which is further illustrated in FIG. 2. The apparatus as illustrated in FIG. 2 further comprises sensors 3a and 3b for measuring ECG. Thus, the apparatus 10 may be an apparatus for combined PPG and ECG measurements, which are tightly synchronized with each other. This may be achieved by the timing device, such as a clock, controlling both the first and second devices. Such a timing device could form a part of the control unit.

The pressure cuff 5 of the apparatus 10 comprises a wrist band 5c having an inner 5a and outer surface 5b and the PPG device 4 comprises sensor 4a arranged on the inner surface 5a of the wrist band 5c. The inner surface 5a is thus intended to contact the wrist as the wrist band 5c surrounds the wrist of the person 2 under investigation. The PPG device 4 further comprises illumination means for illuminating the wrist. Sensor 4a is configured for detecting the changes in light absorption of the illuminated light. Furthermore, the apparatus 10 comprises a sensor 3a on the inner surface 5a of the wrist band 5c. Sensor 3a is configured for measuring the ECG together with another sensor, such as a sensor 3b arranged on the outer surface 5b of the wrist band 5c. Sensors 3a and 3b may be configured such that a circuit is closed as the user puts his or her finger on the outer sensor 3b. Thus, sensor 4a may form the entire PPG measurement unit whereas the ECG is measured using sensor 3a together with a further electrode, such as an electrode in sensor 3b. The PPG device 4 is configured to measure blood volume in the wrist 6 and thereby configured for measuring arrival of the pulse wave as a function of time.

The wrist band 5c further comprises inflatable portions (not shown) and the pressure cuff 5 further comprises a pump 9, such as a manual pump, for inflating the inflatable portions, thereby generating a pressure to the wrist onto which the wrist band 5c is attached. The PPG device 4 may thus measure arrival of the pulse wave as a function of time during inflation of the pressure cuff 5, when a constant pressure is applied to the wrist by the cuff 5, and/or during deflation of the pressure cuff 5.

The system 1 further comprises a control unit 7 configured for receiving information from an ECG unit, such as the ECG unit 3 in FIG. 1a or the ECG sensors 3a and 3b in FIG. 2, and from the apparatus 10, i.e. from pressure cuff 5 and from PPG device 4. An embodiment of a control unit 7 is schematically illustrated in FIG. 1b. The control unit 7 is in this embodiment wirelessly connected to the ECG unit 3 (or ECG sensors 3a and 3b) and to the apparatus 10. The control unit 7, the ECG unit(s) and the apparatus 10 may thus be connected to the same wireless communication network. The control unit 7 comprises a communication interface 7a, such as a transmitter/receiver interface, via which it may receive data from the ECG unit 3 and the apparatus 10, i.e. from pressure cuff 5 and from PPG device 4. The control unit 7 is thus configured for receiving information of the onset of an activity of the heart from the ECG device, receiving information of changes in arrival of the pulse wave from said PPG unit 4 and information about applied pressure on the wrist extremity from the pressure cuff 5.

The control unit 7 is further configured to carry out a method for determining at least one parameter related to the microcirculation function, such as at least one endothelial function parameter, according to embodiments disclosed herein. For this purpose, the control unit 7 may comprise a device having processing capability in the form of processing unit 7b, such as a central processing unit, which is configured to execute computer code instructions which for instance may be stored on a memory 7c. The memory 7c may thus form a computer-readable storage medium for storing such computer code instructions. The processing unit 7b may alternatively be in the form of a hardware component, such as an application specific integrated circuit, a field-programmable gate array or the like.

The control unit 7 is also configured for controlling when to take measurements with the ECG unit 3, and from PPG device 4, i.e. configured for initiating the retrieval of data from the first device 3, the second device 4 and the pressure device 5. The control unit 7 may thus also indicate when to apply a pressure using the pressure device 5. Thus, the control unit 7 is further configured for controlling the initiation of the measuring of the ECG unit 3, the PPG device 4 and the initiation of the applying of a pressure using the pressure cuff 5.

For this purpose, the processing unit 7b may further comprise computer code instructions for sending operational requests to the ECG unit 3 and the PPG device 4.

The system 1 further comprises display means 8 connected to the control unit 7 for displaying on a screen one or several endothelial function parameters determined by the control unit 7.

As an alternative, the control unit 7 may be configured just for receiving the data from the ECG unit 3 and the apparatus 10, i.e. from pressure cuff 5 and from PPG device 4. This data may then be sent to an external unit for further processing. As an example, the data may be transmitted to a storage unit (not shown), which may be a disk drive of a computer. The communication interface 7a may thus be configured to transmit received data from the ECG unit 3, from pressure cuff 5 and from PPG device 4 to a remote storage unit, such as a cloud-based storage unit. A remote software may then be used for assessing the endothelial function parameters from the transmitted data according to the methods disclosed herein.

Consequently, the data received by the control unit may be sent to a computer, and such a computer may have a central processing unit (CPU) and may further be provided with a software for causing the CPU to perform operations so as to determine related to the microcirculation function of a person based on the ECG and PPG data.

The method for determining at least one at least one parameter related to the microcirculation function, such as at least one endothelial function parameter, will be further discussed in relation to FIGS. 3 and 4. The method may be performed by the system 1 as discussed in relation to FIG. 1a, FIGS. 1b and 2 above.

FIGS. 3a-c show how the time (AT) of a pulse wave may be determined. FIG. 3a shows an electrocardiogram determined by the ECG unit 3. As seen in FIG. 3a, the electrocardiogram displays the typical sinus rhythm comprising a QRS complex with major peaks 20. Simultaneously and synchronically as detecting the ECG, a PPG is acquired. The PPG curve from a part of the body, such as a wrist, is displayed in FIG. 3b. From the acquired ECG and PPG signals, the method comprises the step of a) determining an arrival time (AT) of a pulse wave, wherein the AT is the time between the onset of an activity of the heart that produces a pulse wave and the arrival of said pulse wave in a part of the body of said person. In the example of FIG. 3, the AT is determined as the pulse arrival time (PAT), wherein the PAT is the time delay between onset of electrical activation in the ECG and the arrival of the pulse wave in the part of the body. The onset of the electrical activation is in FIG. 3a the onset of the major R peak.

The determined PAT is displayed as a function of time in FIG. 3c. Further, the method comprises b) varying an applied pressure (P) on the part of the body over time, e.g. by inflating the pressure cuff, and determining said PAT as a function of applied pressure and time.

From the acquired data, parameters related to the microvasculature may be determined. Thus, the method further comprises the step of c) determining at least one parameter related to the microcirculation function based on said determination of the PAT and the PAT as a function of applied pressure and time in steps a) and b).

The data obtained in step c) is plotted in FIG. 4, which thus displays the calculated PAT during different applied pressure periods 21. The pressure periods 21 are displayed in the upper graph of FIG. 4, and comprises an increase 21a in applied pressure, a decrease 21b in applied pressure as well as a resting phase 21c. A pressure period is in this example about 50-80 s long, and data of the PAT is acquired during at least three pressure periods.

As further displayed in FIG. 4, different parameters may be extracted from the data that are related to the endothelial function of the person being investigated:

1. Pulse transit time from arteries to capillaries ($PTT_{art-cap}$) in FIG. 4. $PTT_{art-cap}$ is calculated as average PAT when the pressure cuff is completely deflated (under steady state condition) minus the average PAT calculated during high cuff pressures (>70 mmHg). The $PTT_{art-cap}$ may be an important endothelial function parameter since pulse transit time is reciprocal to pulse wave velocity with is directly related to vessel stiffness (according to Moens-Kortweg relation). The higher the $PTT_{art-cap}$ the smaller the stiffness. Increased stiffness of the capillary, reflected in altered pulse transit time may indicate poor endothelial function.

2. Pulse wave transit time overshoot ($\Delta AT$ in FIG. 4). Calculated as highest PAT observed during deflation minus average PAT when the pressure cuff is completely deflated (under steady state condition). $\Delta PAT$ may be an important endothelial function parameter since vasodilating substances (like nitric oxide) will alter vessel stiffness and thereby PAT. Endothelial dysfunction is defined as impaired regulation of vasodilating/vasoconstrictive substances. Lower $\Delta PAT$ indicates impaired endothelial function.

3. Pressure in capillary ($P_{cap}$), which may be determined as the pressure in the pressure cuff at which the PAT shows the highest value (see FIG. 4). $P_{cap}$ may be an important endothelial function parameter since when the pressure cuff is inflated, pressure in the cuff exceeds pressure in capillaries, causing the capillaries to collapse which leads to a decreased PAT. PAT increases when the pressure in the cuff is lower than the capillary pressure. Increased capillary pressure indicates poor endothelial function (i.e. inability to control blood pressure).

4. The dynamical response time of the PAT after occlusion of the capillaries modelled by fitting an exponential decay resulting in dynamical response time constant ($t_{RC}$) (see FIG. 4). $t_{RC}$ may be an important endothelial function parameter since the release of vasodilating and vasoconstrictive substances by the capillaries determines the changes in, i.e. dynamics response of, PAT. A difference dynamic response indicates a different endothelial function. A higher dynamical response time constant ($t_{RC}$) may indicate decreased endothelial function.

Figure 5:
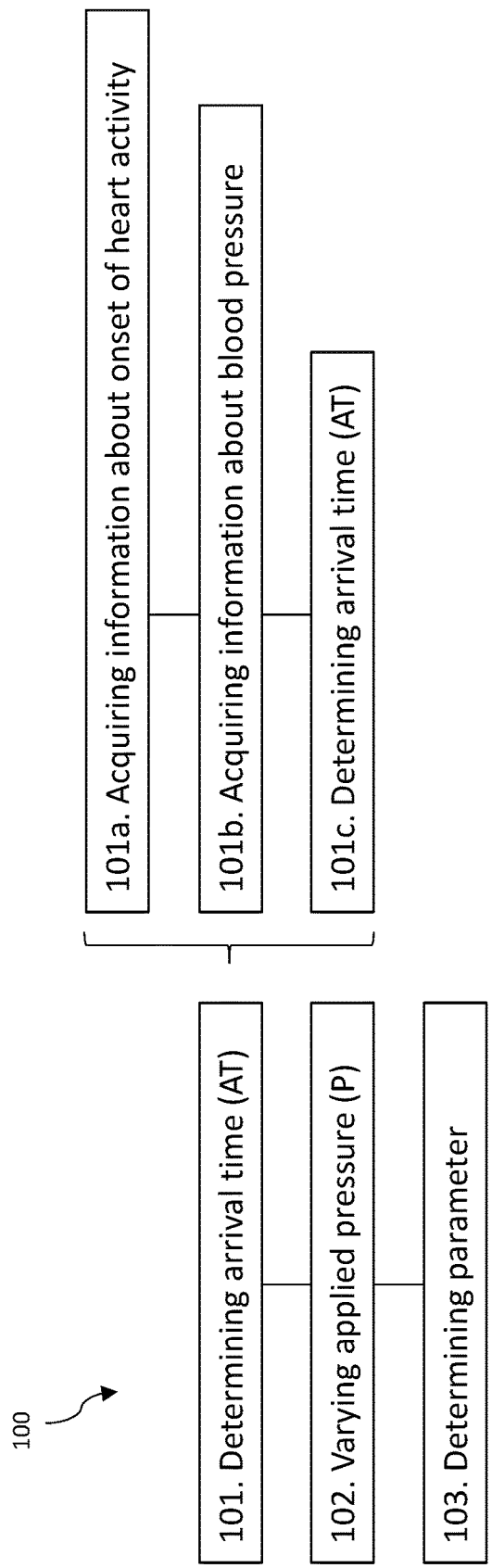
FIG. 5 schematically illustrates a method of the present disclosure.

Furthermore, FIG. 5 schematically shows the general method 100 of the present disclosure for determining at least at least one parameter related to the microcirculation function of a person. The method 100 comprises the steps of determining 101 an arrival time (AT) of a pulse wave, wherein the AT is the time between the onset of an activity of the heart that produces said pulse wave and the arrival of said pulse wave in a part of the body of said person;

varying 102 an applied pressure (P) on said part of the body over time and determining said AT as a function of applied pressure and time; and determining 103 said at least one parameter related to the microcirculation function based on said determination of AT and said AT as a function of applied pressure and time in steps a) and b).

Further, as illustrated in FIG. 5, the step of determining 101 may comprise acquiring 101a information about the onset of an activity of the heart that produces a pulse wave in said person as a function of time; and acquiring 101b information about the arrival of said pulse wave in a part of the body as a function of time during step a1); and determining 101 c the AT from the information from step 101a and 101b.

Figure 6:
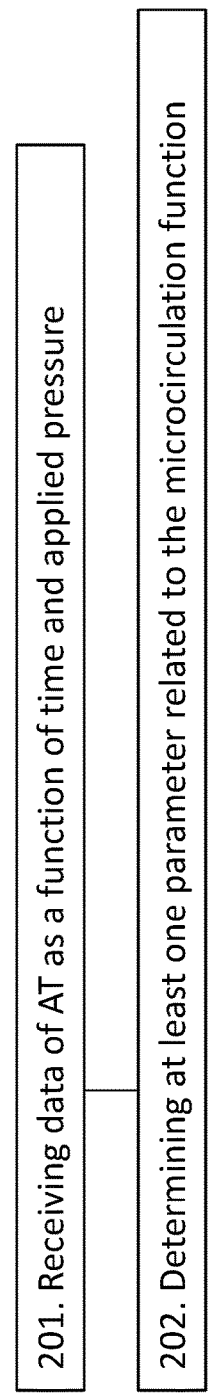
FIG. 6 schematically illustrates a further method of the present disclosure.

As mentioned herein above, the method for determining at least one parameter related to the microcirculation function of a person described above may be embodied as a computer program product comprising a computer-readable storage medium with instructions adapted to carry out the inventive method when executed by a processor. The instructions may thus comprise the method 200 as schematically is illustrated in FIG. 6, i.e. comprising the steps of receiving 201 data of the arrival time (AT) as a function of time and applied pressure; wherein the AT is the time between the onset of an activity of the heart that produces a pulse wave in a person and the arrival of said pulse wave in extremity part of the body of said person and wherein said applied pressure is a pressure applied to said part of the body, and determining 202 at least one parameter related to the microcirculation function from the received data.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A method for determining at least one parameter related to the microcirculation function of a person, said method comprising the steps of:
   a) determining an arrival time (AT) of a pulse wave, wherein the AT is the time between onset of an activity of a heart that produces said pulse wave and arrival of said pulse wave in a location at a microvasculature in a part of a body of said person;
   b) varying an applied pressure (P) on said part of the body over time, wherein the applied pressure (P) compresses at least tissue surrounding the location at the microvasculature in the part of the body, and determining said AT as a function of applied pressure and time; and
   c) determining said at least one parameter related to the microcirculation function based on said determination of AT and said AT as a function of applied pressure and time in steps a) and b).

2. The method according to claim 1, wherein step a) comprises the steps of:
   a1) acquiring information about the onset of an activity of the heart that produces a pulse wave in said person as a function of time; and
   a2) acquiring information about the arrival of said pulse wave in the location at the microvasculature in the part of the body as a function of time during step a1); and
   a3) determining the AT from the information from step a1) and a2).

3. The method according to claim 1, wherein step b) comprises applying external pressure for at least one period, wherein said period comprises an increase in applied pressure and a resting phase.

4. The method according to claim 1, wherein step b) comprises applying external pressure over a time course during which a plurality of pulse waves arrives at said part of the body.

5. The method according to claim 1, wherein step c) comprises determining an average pulse transit time from arteries to capillaries (PTTart-cap); wherein PTTart-cap is the average AT determined in step b) when no pressure is applied to said part of the body minus the average AT from step b) at an applied maximum possible capillary pressure.

6. The method according to claim 1, wherein step c) comprises determining a blood pulse wave transit time overshoot (APAT); wherein APAT is the highest observed AT while decreasing said applied pressure in step b) minus an average arrival time when no pressure is applied in step b).

7. The method according to claim 1, wherein step c) comprises determining a pressure in capillary (Pcap), and wherein Pcap is the applied pressure in the part of the body at which the arrival time of said pulse wave is highest.

8. The method according to claim 1, wherein step c) comprises determining a dynamical response time constant (tRC) of the arrival time of the pulse wave by fitting an exponential decay function to the AT as a function of time during decrease of said applied pressure.

9. The method according to claim 1, wherein a device for acquiring a photoplethysmogram (PPG) is used for measuring arrival of the pulse wave in the part of the body of said person, and wherein a pressure device is used for varying said pressure and said pressure device is a pressure cuff for compressing an extremity of a person and wherein said pressure cuff surrounds the device for acquiring the PPG.

* * * * *